United States Patent
Joos et al.

(10) Patent No.: US 10,300,188 B2
(45) Date of Patent: May 28, 2019

(54) EXTEMPORANEOUS PREPARATION OF AUTOLOGOUS FIBRIN

(71) Applicant: AVANCE MEDICAL SARL, Chavannes-sur-Moudon (CH)

(72) Inventors: Michael Joos, Chavannes-sur-Moudon (CH); Peter Everts, Nuenen (NL)

(73) Assignee: AVANCE MEDICAL SÀRL, Chavannes-sur-Moudon (CH)

( * ) Notice: Subject to any disclaimer, the term of this patent is extended or adjusted under 35 U.S.C. 154(b) by 563 days.

(21) Appl. No.: 14/895,817

(22) PCT Filed: Jun. 2, 2014

(86) PCT No.: PCT/EP2014/061327
§ 371 (c)(1),
(2) Date: Dec. 3, 2015

(87) PCT Pub. No.: WO2014/195252
PCT Pub. Date: Dec. 11, 2014

(65) Prior Publication Data
US 2016/0121036 A1   May 5, 2016

Related U.S. Application Data

(63) Continuation-in-part of application No. PCT/EP2013/061397, filed on Jun. 3, 2013, and a
(Continued)

(51) Int. Cl.
*A61M 1/34* (2006.01)
*A61L 24/10* (2006.01)
*A61L 27/22* (2006.01)

(52) U.S. Cl.
CPC ............. *A61M 1/34* (2013.01); *A61L 24/106* (2013.01); *A61L 27/225* (2013.01);
(Continued)

(58) Field of Classification Search
CPC ...... A61L 24/106; A61L 27/225; A61M 1/34; A61M 1/3403; A61M 2202/0415;
(Continued)

(56) References Cited

U.S. PATENT DOCUMENTS

| | | | |
|---|---|---|---|
| 5,601,727 A | 2/1997 | Bormann et al. | |
| 6,010,627 A | 1/2000 | Hood, III | |

FOREIGN PATENT DOCUMENTS

| | | |
|---|---|---|
| EP | 0733378 | 9/1996 |
| EP | 1155706 | 11/2001 |

(Continued)

OTHER PUBLICATIONS

International Search Report for PCT/EP2014/061327, Comppleted by the European Patent Office on Jan. 29, 2015, 7 Pages.

*Primary Examiner* — John Kim
(74) *Attorney, Agent, or Firm* — K&L Gates LLP

(57) ABSTRACT

An Autologous fibrin is prepared extemporaneously from either a full blood sample or a prepared sample of poor platelet plasma wherein the latter is subjected to a dedicated treatment and combined isolation process performed by a removable single-use device wherein blood or plasma components are separated and subsequently treated individually to be eventually combined by the user outside the system. The system includes a platform and a removable single-use device both being designed to cooperate mechanically.

7 Claims, 2 Drawing Sheets

Related U.S. Application Data continuation-in-part of application No. PCT/EP2013/067040, filed on Aug. 14, 2013.

(52) U.S. Cl.
CPC ... *A61M 1/3403* (2014.02); *A61M 2202/0415* (2013.01); *A61M 2202/0425* (2013.01); *A61M 2202/0449* (2013.01); *A61M 2205/12* (2013.01); *A61M 2205/3306* (2013.01); *A61M 2205/50* (2013.01)

(58) Field of Classification Search
CPC .. A61M 2202/0425; A61M 2202/0449; A61M 2205/12; A61M 2205/3306; A61M 2205/50

See application file for complete search history.

(56) References Cited

FOREIGN PATENT DOCUMENTS

| | | |
|---|---|---|
| EP | 0877632 | 3/2003 |
| EP | 1625861 | 2/2006 |
| EP | 1420833 | 6/2010 |
| EP | 2520316 | 11/2012 |
| WO | 0016872 | 3/2000 |
| WO | 2009031990 | 3/2009 |
| WO | 2010019317 | 2/2010 |

EXTEMPORANEOUS PREPARATION OF AUTOLOGOUS FIBRIN

CROSS-REFERENCE TO RELATED APPLICATION

This application is the U.S. national phase of PCT Application No. PCT/EP2014/061327 filed on 2 Jun. 2014, which claims priority to PCT Application No. PCT/EP2013/061397 filed on 3 Jun. 2013, and PCT Application No. PCT/EP2013/067040 filed on 14 Aug. 2013, the disclosures of which are incorporated in their entirety by reference herein.

FIELD OF THE INVENTION

The invention relates generally to the preparation of tissues and cells including a combination of fibrinogen and thrombin. The invention refers more particularly to a system as well as to a device designed for the isolation of blood or plasma protein components and their use, in particular the isolation and concentration of plasma fractions rich in fibrinogen and thrombin from a single blood donor and their subsequent combination to afford e.g. autologous fibrin glues or fibrin gels or as a 3D fibrinous matrix for tissue and cell engineering purposes.

BACKGROUND OF THE INVENTION

Tissue adhesive in the form of fibrin glues and sealants have been proposed for use to control bleeding, seal wound edges and to promote wound healing in a variety of traumatic and surgical situations. Furthermore fibrin sealants can be used to act as a biological matrix to facilitate and enhance cell survival, cell differentiation and cell proliferation, with emphasis on growth factors and stem cells. Fibrin glues or fibrin gels contain fibrinogen and thrombin which, when mixed together, form a solidified fibrin mesh of fibers, the basic substance of strength in hemostasis or clotting. Fibrin is used intra-operatively to affect hemostasis, sealing of wound edges or used as an adhesion prevention barrier.

In Europe and elsewhere commercial fibrin glues were prepared from fibrinogen and thrombin obtained from either pooling plasma cryoprecipitate from multiple human donors or from animal sources, e.g. Bovine. These products are prepared using laboratory drug regulated manufacturing processes including the need for pasteurization and filtration in order to eliminate harmful pathogens which might be transferred to the patient from such sources.

A further proven risk of these technologies is the risk of immune reaction originating from constituent parts associated to such pooled plasma sources. In addition the technologies are complicated by cold storage logistics, lengthy peri-operative processing times and cost especially at higher volumes. These reasons have caused such products to be used with extreme caution or withdrawn altogether.

In order to avoid the risk associated with pooled plasma sources, autologous fibrin glues, sealants or gels have been proposed where fibrinogen and thrombin are obtained from a single donor. Some of these fibrin products, however, had to rely on the combining of autologous fibrinogen with e.g. bovine thrombin, and thus still suffered from the risk or deficiencies associated with non-human products, e.g. an immune response against bovine plasma proteins.

For these reasons improved fibrin products and means for their preparation, where the fibrinogen and the thrombin components, were isolated from a single human donor blood or plasma sample for the use on that same donor have been proposed.

Several systems, tools or devices and methods as well have been brought forward and, at least for some of same, subsequently launched in order to satisfy this type of yet unmet medical need.

EP 0877 632 B1, for example, refers to a method for preparing stepwise autologous fibrin glue for surgical use and comprising centrifugation of the blood sample to afford a supernatant consisting mainly of plasma including fibrinogen, concentrating fibrinogen in the plasma fraction by means of centrifugation and subsequent filtration and eventually freezing the concentrated plasma before use. Fibrin glue is obtained by mixing the thawed concentrated plasma fraction with a "suitable starter", indeed thrombin. Centrifugation is performed using interconnected plastic pouches constituting a closed system and the transfer of specific plasma fraction is indeed performed manually.

EP 1155 706 A1 discloses an apparatus for producing "clinically ready fibrinogen of high concentration" and discloses a closed system, in fact an apparatus provided with means for receiving blood concentration from a patient, a plasma membrane separator to extract and separate the plasma from undesirable components, a second membrane separator to provide separation of fibrinogen.

A vacuum pump is connected to the fibrinogen collector; a freezer is used to provide adjustable temperatures to the various plasma fractions; communication means comprise at least one peristaltic pump to maintain plasma transport within the closed system. According to a specific embodiment the system further comprises a mixer to mix fibrinogen with an adequate concentration of autologous thrombin and calcium salt to form the fibrin glue.

EP 1420 833 refers to a system (apparatus) for producing an autologous platelet gel which makes use of an autologous anti-coagulated blood sample as starting material and comprises, among others, a first vessel comprising means for activating the blood components which then provides coagulated blood components and expresses eventually thrombin therefrom.

The said first vessel is fitted with an external filter having a pore size that allows thrombin to pass through it selectively, the filtered thrombin being then mixed with a separate portion of autologous blood components like red blood cells, white blood cells, platelet rich plasma (PRP), platelet poor plasma (PPP) which all result from the centrifugation of the initial autologous blood sample and which are stored in a second vessel, to form autologous platelet gel.

All these solutions and their equivalents present some drawbacks: the simplest systems, e.g. as defined in EP 0877 632 B1, present the risks of disturbing the sterility inherent to hand manipulations, do not produce sufficient quantities to satisfy the needs of large surgeries, are impractical to operate during a surgical procedure, are too costly both in peri-operative labor input and materials and take too long thus not allowing the use of such systems during the course of the procedure.

Closed systems like those mentioned here above, or their equivalents, proved to be excessively complex to handle and to monitor, to be highly expensive in their use especially due to the necessity to clean and to decontaminate (if indeed possible at all) and to sterilize most of their parts for subsequent re-use and were therefore not adopted leaving ready to use recombinant or animal based products, stored frozen, as only practical, cost-economic technologies for surgeries requiring only small volumes of fibrin today thus still leaving an unmet medical need in those procedures, especially cardiac and orthopedic, requiring larger volumes >10 ml.

The invention obviates adequately all the obstacles still met in surgical process and responds to an obvious unmet medical need. The invention is defined in the claims appearing here below.

SUMMARY OF THE INVENTION

An object of the invention is a system useful for the treatment or the isolation of plasma or blood components including a specific support platform arranged to cooperate with a removable single-use device and which comprises means of mechanical actuation, means of mechanical or electro-magnetic or visual contact, means of thermal transfer, shaking means and means of control and command as well as a removable single-use device as defined here below.

Another object of the invention is a removable single-use device for use in the above system and comprising: interconnected treatment chambers, storage chambers; means for transferring the flows of liquids from a chamber to another one, respectively the flows of liquids or gas from the outside to the inside of device 2 or from the inside of device 2 to the outside, and means for controlling the flows of liquids from a chamber to another one, respectively flows of liquids from the outside to the inside of device 2 or from the inside of device 2 to the outside.

Another object of the invention is the use of the said system for the preparation of at least two separate autologous plasma fractions enriched in thrombin and fibrinogen respectively.

Still another object of the invention is a device for enriching the fibrinogen content of a plasma fraction comprising three separate chambers connected in such a way to establish a self-regulating closed circuit; each of them being fitted with an inlet and/or an outlet and suited for performing either individually in a dedicated container or embedded in the system referred to here above.

Still another object of the invention is the use of the said system for the extemporaneous preparation of autologous fibrin.

Still another object of the invention is the use of the said system for the preparation of a 3D fibrin cell preservation and cell growth and proliferation matrix.

DETAILED DESCRIPTION OF THE INVENTION

Figure 1:
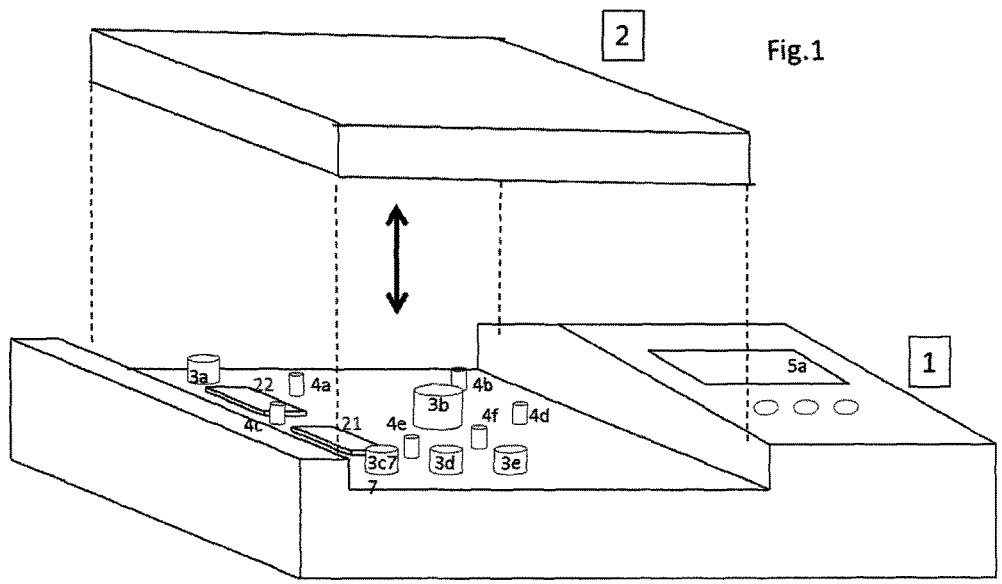
FIG. 1 is a perspective view showing platform 1 fitted with the dedicated means which shall cooperate with corresponding means embedded in device 2.
Figure 2:
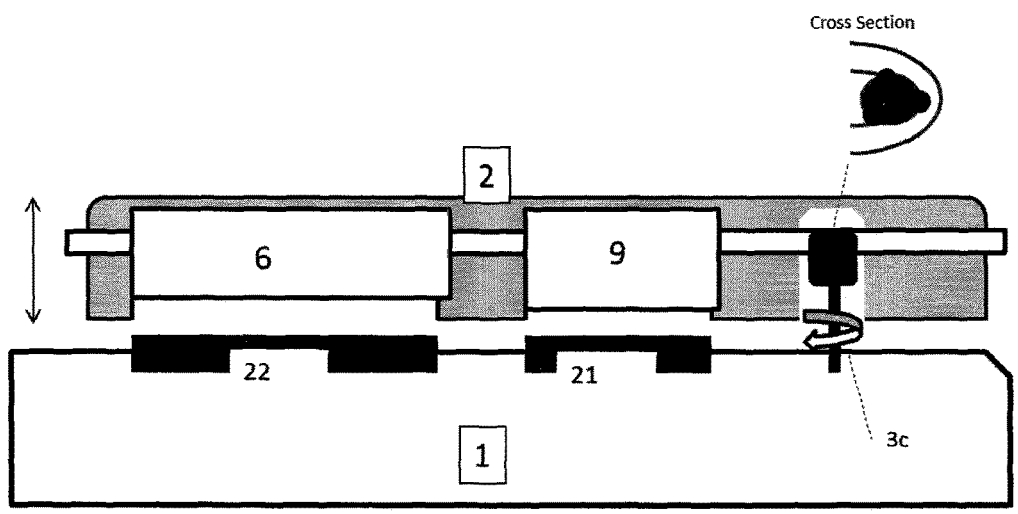
FIG. 2 is a partial section view of both platform 1 and device 2.

The system according to the invention comprises first the platform 1. This one includes, among others, mechanical means of activation 3a, 3b, 3c . . . , for example vertically connected axes each arranged in or connected to an embedded engine (not illustrated) and ordered to pull the corresponding counterpart of a pump, such a peristaltic pump 3a, 3b, 3c . . . , e.g. located inside the removable device 2.

Each of the said engines pulling the above mentioned axes is individually controlled, for putting on or off the said pumps as well as for their rotation speed for example. This control is made by means of the centralized control and command unit 5a, such a microprocessor for example, according to a predefined and preset protocol: the said engines can be thus managed substantially automatically or, alternatively, according to own choices of the user. In this last case, the instructions of the user are transmitted throughout the aforementioned platform by means of for example a touch-sensitive screen 5a.

The platform 1 also includes mechanical, electromagnetic or even visual contact means 4a, 4b, 4c . . . . These means can include for example pressure sensors, heat sensor or visible or infrared light detectors. These means of contact 4a, 4b, 4c . . . serve in particular to check and control the positioning (OPEN/CLOSED or ON/OFF) of valves 14a, 14b, 14c . . . located in the removable device 2 and, consequently, serve to manage or to regulate the various transfers of fluids throughout said device 2, for example from one chamber to another one or from the outside of device 2 towards an inside chamber like treatment chamber 6 or 10 or vice versa.

The platform 1 further includes means of thermal transfer 21 or 22, generally placed directly below the chambers subject to thermal transfer, in particular storage chamber 9 or mixing chamber 6. These means serve as well to warm than to cool the content of one or several of the chambers dedicated to that purpose and, also, to maintain the fluid content of these chambers at the desired temperature for a prolonged period if necessary.

The platform 1 further comprises shaking means 22, generally placed directly below the chambers subject to shaking or agitation, in particular treatment chamber 6. Shaking means are such to perform by mere mechanical contact with the relevant location in the bottom of device 2, i.e. below chamber 6 for example or, alternatively, distal therefrom and by means of a rotating metal plate pulling a magnet placed in said chamber 6. The monitoring and the actuation of said shaking means is driven by means of the centralized control and command unit 5a.

These means of thermal transfer are also dependent on the control and command unit 5a mentioned here above and the temperatures or the selected temperature variations can be set in advance according to a pre-established and preset protocol or, alternatively, along to the progression of the fluid flows moving inside the removable device 2, i.e. whereby the necessary instructions are provided step by step by the user to said control and command unit.

According to the invention each of the chambers of device 2 is fitted with respective inlets 7a, 7b, 7c, 7d and outlets 8a, 8b, i.e. connecting devices generally used in the art to lock standard syringes to any pipe or pouch or bottle used in the medical or surgery domain.

Inside device 2 the chambers are interconnected by means of standard pipes, preferably flexible plastic tubing used conventionally for blood or plasma transfusion. This tubing 444, 444a, 444b, . . . are either linear, circular or branched depending on their location and their functionality as well.

Inside both linear and branched pipes 444, 444a, 444b, . . . there are located valves 14a, 14b, 14c, 14d, 14e, 14f, 14g, 14h, 14i, . . . . These valves represent the means necessary to monitor various transfers of fluids throughout device 2, from one chamber to another one and from the outside of device 2 to the inside, e.g. when the starting PPP sample is introduced into treatment chamber 6 or 10, or when thrombin is leaving storage chamber 9 to be transferred outside device 2 and when, the enriched fibrinogen plasma fraction is leaving simultaneously mixing chamber 12 to be transferred outside device 2.

Valves 14a, 14b, 14c, . . . are usually embedded mechanical or electro-magnetic valves as frequently met in medical devices used e.g. in blood transfusion and they are arranged to cooperate with the contact means mentioned here above. They can further comprise light sensors which easily detect if and when a pipe or a chamber is either full or empty. Pressure sensors can also act in a similar way.

According to a preferred embodiment of the invention actuating means 13 comprise peristaltic pumps 13a, 13b, 13c, 13d, 13e, . . . arranged to cooperate with the corresponding engines such as those referred to above. The said cooperation is such that the mechanical actuating modalities of device 1 can enter the outer casing/housing of the disposable device at pre-designated design openings but are at all times in contact with the external aspects of the chambers and tubing of the internal closed circuit system so as to not come in direct contact with their sterile or biological content which would otherwise lead to contamination and risk of transfer of disease or infection.

The system of the invention also comprises means of thermal transfer 21, ensuring either the heating or the desired cooling of the plasma fractions temporarily left in a specific chamber. Heating and/or cooling can be performed by means of a suitable electric or other device, generally located at or close to the interface between platform 1 and device 2 but resident on platform 1 Heat transfer occurs usually by conduction, i.e. by mere physical contact between the relevant portions of platform 1 and device 2 involved.

The system of the invention enables separating and subsequently treating specific blood or plasma fraction and, eventually, recombining extemporaneously duly selected blood or plasma components, in particular thrombin and fibrinogen generated from a single blood sample to afford fibrin, autologous fibrin more specifically.

The sequence of the operations carried out when using the system of the invention is briefly described here below.

Whole blood is previously centrifuged and separated into three distinct fractions: red blood cells (RBC), platelet rich plasma (PRP) and platelet poor plasma (PPP). This centrifugation can be performed at point of care or several hours or days before surgery or tissue engineering or injection purposes, or during the surgery or procedure as required e.g., by means of an external blood components separator, each of these fractions being then stored separately, in usual conditions.

The fraction consists of concentrated platelets, stem cells, tissue scaffold, etc. is kept temporarily in a separated vessel with the aim of its optional or delayed administration to the blood donor if applicable. In that purpose a standard syringe containing the desired amount of fraction to administer to the blood donor will be connected in due time to mixing chamber 12 by a tip 7c and a pipe portion 11 cooperating with the pump 13d.

A first portion of PPP is introduced into treatment chamber 6 via inlet 7a, by means of a standard syringe or other means; the plasma fluid is pulled in direction of said chamber 6 by means of peristaltic pump 13b while valve 14a is temporarily set to allow movement to tubing 444a and closed off to 444b whereby avoiding any fluid transfer through tubing 444b which is leading to the chamber 10. The valve 14i is simultaneously left closed towards said chamber 6 while avoiding any fluid transfer through pipe portion 444c leading to mixing chamber 9. Valve 14h is simultaneously set so that it opens towards 444 but is closed towards chamber 10.

A predefined portion of catalyst or reagent is then introduced into treatment chamber 6 via inlet 7b, e.g. by means of a syringe and the reagent mixture passed over negatively charged spheroids aided with agitation through shaking and thermal transfer from 22 on system 1 or by other means over a predefined period to afford thrombin rich plasma separation (rich being defined as e.g. >2× patient's own baseline). Valves 14a, 14g and 14i as well remain closed in order to avoid any other fluid transfer inside the device during this operation. The plasma fraction containing thrombin is then transferred through a filter 888 filtering out anything above molecular weight 6000, into tubing 444c to storage chamber 9, with valve 14i open for facilitation of movement, and stored therein at optimal temperature provided by thermal transfer from 21 on system 1 before its subsequent transfer to e.g. a double body syringe currently used in the art, via outlet 8b. A one way air filter valve 555a facilitates the priming of fluid into the tubing between chamber 9 and exit 8b by eliminating air in that part of tubing prior to entering syringe 18a.

A second portion of PPP is introduced into treatment chamber 10 aided by 13b via same inlet 7a this time valve 14a opening towards 444b and shutting towards 444a and valve 14h open to 444 and inlet 7a while at same time closed to 444e where the PPP is subject to a concentration which can be carried out as described here after. As the PPP enters the circuit the air present therein pushed forward in the circuit and expressed into chamber 333 through valve 14b to effect priming of the circuitry removing any remnant air. Simultaneously chamber 16, which is an inflatable bag, is filled with a certain volume of PPP. The water initially present in the PPP fraction is progressively filtered off by means of hollow fibers with distinct cross-membrane pressure gradients e.g. a filter inside chamber 10 and subsequently moved with help of the circuit pressure created by pump 13b and placed into expandable chamber 333 via one-way valve 14b. Chamber 333 is initially a collapsible bag or vacuum filled container which receives air from initial priming of circuit with PPP and subsequently the water from the filtering process.

The open pipe connection undergoes a progressive aspiration which is applied from exit 14b e.g. by means of a negative pressure device induced through by example mechanical or other means on chamber 333. Simultaneously as water leaves the circuit through the filter the remaining volume of fluid/gas in the circuit is reduced. To accommodate for such a reduction in fluid in the circuitry, and to avoid a collapse of the tubing from the negative pressure this could cause, a variable size/volume chamber 16 is installed. During the filtration process as described valve 14h allows fluid to pass into and out of chamber, via 444e and 444 while being blocked off to tubing with inlet 7a.

One gets, eventually, over a predefined period, a concentrated PPP fraction having a high content of fibrinogen (e.g. >2.5× patient blood baseline values) which is then transferred directly to mixing chamber 12 and out through 8a while valve 14f is open. As concentrated fibrinogen fraction is expelled via outlet 8a into a standard syringe of the art valve 14c is open to tubing 444b but closed off to tubing 444d all the while being pulled through by pump 13e or 13b. In order for the circuit to purge it of its content air must be introduced through an air-filter 555 (to avoid negative vacuum pressure) and valve 14d must be set closed towards tubing 444b and open towards tubing 444d. Air then is able to enter the circuit to allow liquid content of the circuit to be expelled into mixing chamber 12 and into syringe through outlet 8a.

Provided red blood cells (see above) or a solution of any suitable chemical reagent or pharmaceutical component, such as an additive, or any additional biological tissue component such as fat, bone marrow concentrate or stromal vascular fraction among other, has to be added to the fibrinogen plasma fraction, peristaltic pump 13d is then started up rotating to take away the desired amount of additive from its container, i.e. a syringe connected to standard connector inlet 7c and pulling said additive into mixing chamber 12. The simultaneous and computer steered action of pumps 13e or 13b, 13d and 13c will determine the ratio and thus mixtures of substances to be expelled through 8b and 8a into a double body syringe system with first syringe attached to outlet 8b and second syringe attached to outlet 8a. For purposes of further understanding these syringes are of different size and therefore when depressed at same rate will deliver a further exact ratio of mixing of substance from outlet 8b with that of outlet 8a. It is this ratio combination of fibrinogen and thrombin rich plasma fractions that will create the fibrin as the two mix e.g. on the wound/tissue surface.

The configuration of this mixing chamber 12 is generally such that the mixture of the two plasma fractions at stake is made by simple flow of components but may incorporate further means of mechanical mixing inside said chamber 12.

Autologous fibrin, eventually, is generated spontaneously from thrombin and fibrinogen when the content of each of the above cylinders is pushed off by the user.

Another embodiment of the invention consists in a device for enriching the fibrinogen content of a plasma fraction comprising three interconnected chambers each of them fitted with an inlet and/or an outlet, connecting means for transferring fluid flows from one chamber to another one provided with either means for controlling said fluid flows and/or means for moving said fluid flows from one chamber to another one or to the outside.

The latter comprises first a treatment chamber 10 provided with internal filtering means, a first expandable storing chamber 333 connected to chamber 10, and a second expandable chamber 16 connected to chamber 10 in such a way to establish a closed circuit between said chambers 10, 333 and 16.

Such an interconnection enables an easy and highly performing self-regulation or self-adjustment of the volume/content of the whole circuit involved in the operations.

In accordance with a preferred embodiment, chambers 10 and 333 are connected each with the other one by means of a pipe comprising a one-way valve, e.g. valve 14b whereas the portion of the closed circuit involving chambers 10 and 16 is fitted with pipes comprising multidirectional valves, e.g. 14h, 14d . . . .

Both expendables chambers 16 and 333 can be made of either inflatable plastic pouches or bags or of simple syringes of the art.

The means provided for moving fluid flows from one chamber to another one comprise usually a peristaltic pump e.g. 13b or 13e, similar to those used in the above mentioned system.

The said device further comprises means for electromagnetic or visual contact and means for control and command similar to those used in the above mentioned system.

Eventually, the said device is suited for performing either individually in a dedicated container or embedded in the system referred to above.

Figure 3:
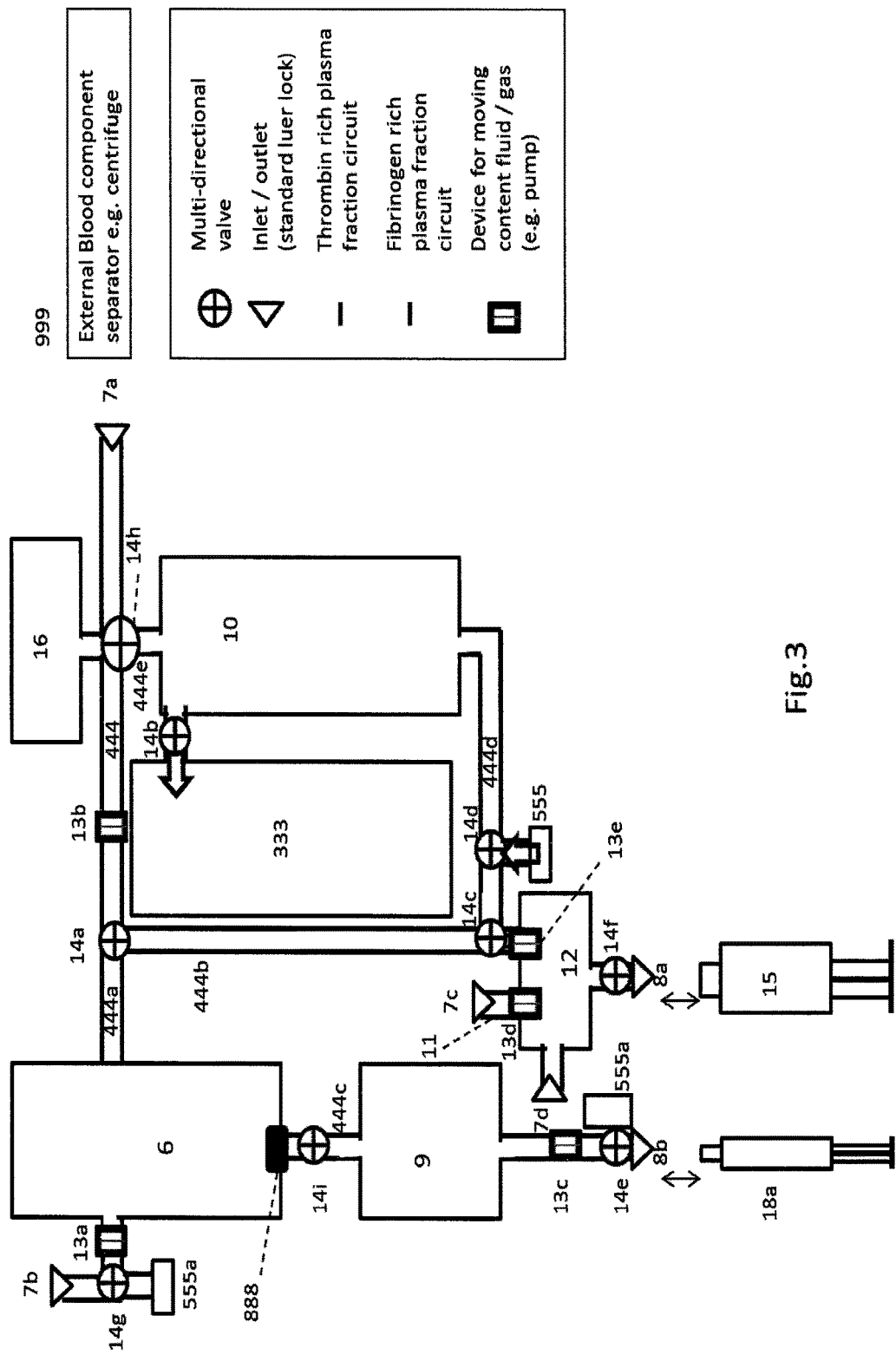
FIG. 3 is a schematic representation of the inside of device 2.

Example 1 (With Reference to FIG. 3)

Isolation and Purification of Thrombin and Fibrinogen from Plasma a) 180 ml of whole human blood containing required amount of anti-coagulant is centrifuged and separated into three distinct fractions: 1) ca. 70 ml of red blood cells (RBC); 2) ca. 5 ml of concentrated platelet rich plasma (PRP) and 3) ca. 105 ml of platelet poor plasma (PPP) after ca. 20 min. during the patient treatment procedure.

As required by the treating physician a syringe containing all or a portion of the subsequent (diluted or undiluted) PRP fraction shall be placed in a syringe with standard "luer-lock" connection to mixing chamber 12 by inlet 7c and a pipe portion cooperating with the pump 13d.

b) A first portion of 12 ml of PPP is introduced into treatment chamber 6 via inlet 7a, by means of for example a syringe connected to standard "luer-lock" inlet 7a; the plasma fluid is pulled in direction of said chamber 6 by means of peristaltic pump 13b while valve 14h is temporarily left open to tubing 444 but and chamber 16 but closed towards chamber 10 in order to avoid any fluid transfer through the tubing towards chamber 10. Simultaneously valve 14g is closed towards inlet 7b but open towards one way valve air filter outlet 555a. This allows the filling of tubing and chamber by displacing the air contained therein before use. Simultaneously valve 14i is closed during this process to avoid fluid moving prematurely into chamber 9.

A predefined portion of a reagent, for example 2.4 ml ethyl alcohol, 1.15 wt % $CaCl_2$, is introduced into treatment chamber 6 via inlet 7b, e.g. by means of syringe and pulled through by pump 13a or injected by simple depression of the reagent syringe. The reagent and primed contents of chamber 6, which contains for example negatively, charged glass spheroids, and previously introduced PPP are mixed together by vibration agitation introduced externally from 22 of system 1 the device platform interface and then left to react for approximately 15 min. The plasma fraction rich in thrombin is then transferred through a filter 888 via valve 14i through tubing 444c into storage chamber 9 and stored therein at room temperature or chilled to 6 degrees Celsius if stored for longer durations (e.g. >45 mins).

c) A second portion of 105 ml PPP is introduced into treatment chamber 10 via inlet 7a and pipe portion 444, 444b and 444d via open valves 14h, 14a, 14c and 14d and wherein the PPP is then subject to a concentration which is carried out as follows: the water initially present in PPP is progressively filtered off by means of for example a hemodialysis plasma filter with filtering membranes where after the filtered water flows progressively out of said chamber 10 into the external reservoir 333.

The PPP concentration process happens via multiple passes of the PPP over the filtering membranes of chamber 10 in a closed circuit. For this a closed circuit has to be established which allows the volume of PPP to reduce as water is eliminated from it through one-way valve into chamber 333. Therefore the circuit comprising of 14h, tubing 444, pump 13b, valve 14a, tubing 444b, valve 14c, 14d, tubing 444d and chamber 10 must first be primed with PPP expelling all air in the circuit through valve 14b into chamber 333. To do this pump 13b activates and valves 14a, 14h, 14d, 14c turn in direction of circuit described with valve 14b open towards chamber 333. Thereby as PPP is pulled into inlet 7a from outside container/syringe the air in the system is expelled into chamber 333 which is made from an expandable material so as to inflate as air and subsequently water from the filtering process are expelled therein. Simultaneously valve 14h (being a 3 way valve) is also open to chamber 16. Chamber 16 is a variable chamber which as water exits the circuit and reduces in size to prevent buildup of negative pressure or vacuum from being created.

One gets, eventually, over a period of approx. 5-10 minutes, a concentrated PPP fraction having a high content of fibrinogen, i.e. approx. 2.5-5 times higher than patient's own baseline. Once the required concentration is reached, as determined by sensors or timing, the contents can be expelled into mixing chamber 12 and subsequently into a syringe through outlet 8a. To do this the reverse of the priming, being purging, of the tubing system must occur. That requires the entry of air into the circuit without which the fluid could not be expelled. For this to happen, the same circuit as already described must reduce in volume consequently at the same ratio as the concentration i.e. the volume of the expelled water. Chamber 16 reduces in size as filtration continues. This can be done simply by attaching a syringe whereby the plunger will automatically move up or down with the direction of the PPP priming or concentration processes.

d) Provided platelet rich plasma, bone marrow derived stem cell concentrates, fat tissue, pharmaceuticals or any other substance are required to be mixed with the fibrinogen (for subsequent activation by the thrombin and/or to be embedded in the fibrin matrix) then these can be attached via a pre-filled syringe containing said substances to inlet 7c. The control system of the device will allow exact ratios of said substances to be mixed, in accordance with clinical requirements and protocols, with the fibrinogen and subsequently with the thrombin. In addition a simple rubber needle entry port, 7d, is also provided for addition of further pharmaceuticals if required.

Then, following user's instruction, peristaltic pumps 13c, 13d and 13e are started up simultaneously while 13b is pushing the fibrinogen plasma fraction referred to above out of the mixing chamber 12 into the first cylinder of a double body syringe provided with a single exit, whereas pump 13c is transferring by suction the stored thrombin out of the storing chamber 9 and transfers the latter into the second cylinder of the double body syringe provided with a single exit 8b. All of these actions can also be done by pulling on the syringe handles of 18a or 15 in order to create negative pressure onto the circuitry and thereby pull the contents into syringe as required, manually, by the operator. In such a case a mechanism to ensure free movement of valves and pumps is envisaged.

Autologous fibrin, eventually, is generated spontaneously from thrombin and fibrinogen when the content of each of the above cylinders is pushed off by the user.

Example 2 (With Reference to FIG. 3)

Enrichment of Platelet Poor Plasma (PPP) in Fibrinogen

A portion of PPP is introduced into treatment chamber 10 aided by 13b via same inlet 7a this time valve 14a opening towards 444b and shutting towards 444a and valve 14h open to 444 and inlet 7a while at same time closed to 444e where the PPP is subject to a concentration which can be carried out as described here after.

As the PPP enters the circuit the air present therein pushed forward in the circuit and expressed into chamber 333 through valve 14b to perform priming of the circuitry removing any remnant air. Simultaneously chamber 16, which is an inflatable bag or a simple syringe, is filled with a certain volume of PPP. The water initially present in the PPP fraction is progressively filtered off by means of hollow fibers with distinct cross-membrane pressure gradients e.g. a filter inside chamber 10 and subsequently moved with help of the circuit pressure created by pump 13b and placed into expandable chamber 333 either direct or via one-way valve 14b. Chamber 333 is initially a collapsible bag or vacuum filled container which receives air from initial priming of circuit with PPP and subsequently the water from the filtering process.

The open pipe connection undergoes a progressive aspiration which is applied from exit 14b e.g. by means of a negative pressure device induced through by example mechanical or other means on chamber 333. Simultaneously as water leaves the circuit through the filter the remaining volume of fluid/gas in the circuit is reduced. To accommodate for such a reduction in fluid in the circuitry, and to avoid a collapse of the tubing from the negative pressure this could cause, a variable size/volume chamber 16, which can be a simple syringe, is installed.

During the filtration process as described valve 14h allows fluid to pass into and out of chamber 16, via 444e and 444 while being blocked off to tubing with inlet 7a.

One gets, eventually, over a predefined period, a concentrated PPP fraction in chamber 10 having a high content of fibrinogen (e.g. >2.5× patient blood baseline values) which is then transferred directly out and the concentrated fibrinogen PPP fraction is expelled via outlet 14c into a standard syringe of the art.

The invention claimed is:

1. A removable single use device for treatment and/or isolation of plasma or blood components, the device comprising an apparatus configured for enriching a fibrinogen content of a plasma fraction, the apparatus comprising:
    interconnected chambers comprising a filtering chamber, a first expandable chamber and a second expandable chamber, each of the interconnected chambers fitted with an inlet and/or an outlet, the apparatus further comprising at least one transfer means selected from the group consisting of (i) means for controlling a flow of fluids and (ii) means for moving the fluids, the at least one transfer means configured to transfer the fluids from one of the interconnected chambers to another one of the interconnected chambers or to the outside of the device; and
    a circuit loop comprising the interconnected chambers, a first tubing leading to the inlet of the filtering chamber, a second tubing extending from the outlet of the filtering chamber, and a plurality of valves comprising a first valve, a second valve, a third valve and a fourth valve, the second tubing comprising the third and fourth valves,
    wherein the first valve is configured to selectively connect to a first inlet of the device, the second expandable chamber, the first tubing and the second tubing,
    wherein the filtering chamber is provided with internal filtering means configured to separate water initially present in the plasma fraction from the plasma fraction, and the plurality of valves are configured for controlling the flow of the plasma fraction along the circuit loop such that the circuit loop can allow multiple passes of the plasma fraction over the filtering means, wherein the first expandable chamber is connected to the filtering chamber by the second valve, and the second valve directs the water initially present in the plasma fraction from the filtering chamber to the first expandable chamber, and the second expandable chamber is connected to the circuit loop and the filtering chamber to establish a closed circuit between the filtering chamber the first expandable chamber and the second expandable chamber.

2. The device according to claim 1 wherein the filtering chamber is connected to the first expandable chamber via a one-way valve that is the second valve.

3. The device according to claim 1 wherein the at least one transfer means comprises the plurality of valves which comprise multidirectional valves allowing connection of the filtering chamber and the second expandable chamber to form the closed circuit.

4. The device according to claim 1 wherein the means for moving the fluids comprise a peristaltic pump.

5. The device of claim 1 which further comprises means for electromagnetic or visual contact and means for control and command, and the device is configured for encasing in a dedicated container.

6. The removable single use device of claim 1, wherein the apparatus is configured to be connected to the outside of the device by (a) the first inlet connected to the first valve of the circuit loop and (b) a first outlet connected to the third valve of the circuit loop by a mixing chamber, the device further comprising:

a first chamber of treatment configured to be connected to the outside of the device by a first channel comprising the first inlet and the fourth valve of the circuit loop, by a second channel comprising a second inlet, and by a third channel comprising an outlet filter, a storage chamber and a second outlet, wherein the first chamber of treatment is also connected to peristaltic pumps configured for moving liquids from one of the interconnected chambers to another one of the interconnected chambers.

7. The device of claim 6, wherein the second expandable chamber is configured to reduce in size to prevent a negative pressure build-up as the water initially present in the plasma fraction leaves the circuit loop causing a volume of the plasma fraction to reduce.

* * * * *